(12) United States Patent
Mainguet

(10) Patent No.: US 7,385,381 B1
(45) Date of Patent: Jun. 10, 2008

(54) SENSOR MANUFACTURE WITH DATA STORAGE

(75) Inventor: Jean-François Mainguet, Grenoble (FR)

(73) Assignee: Atmel Switzerland, Fribourg (CH)

( * ) Notice: Subject to any disclaimer, the term of this patent is extended or adjusted under 35 U.S.C. 154(b) by 0 days.

(21) Appl. No.: 11/682,563

(22) Filed: Mar. 6, 2007

(51) Int. Cl.
*G01N 27/00* (2006.01)
*G06K 9/00* (2006.01)
*G11C 11/00* (2006.01)

(52) U.S. Cl. .................. 324/71.1; 365/129; 382/124

(58) Field of Classification Search ............... 324/71.1; 365/129; 382/124
See application file for complete search history.

(56) References Cited

U.S. PATENT DOCUMENTS 6,289,114 B1 9/2001 Mainguet
6,459,804 B2 10/2002 Mainguet

*Primary Examiner*—Evan Pert
(74) *Attorney, Agent, or Firm*—Fish & Richardson, P.C.

(57) ABSTRACT

A biometric sensing device includes a sensor manufacture for sensing a biometric stimulus. The sensor manufacture is also configured to persistently store data electronically, such as security data.

19 Claims, 5 Drawing Sheets

SENSOR MANUFACTURE WITH DATA STORAGE

CROSS-REFERENCE TO RELATED APPLICATION

This Application is related to Application Ser. No. 11/682,545, entitled "Sensor Manufacture with Data Storage," filed on Mar. 6, 2007, the disclosure of which is incorporated herein by reference.

BACKGROUND

This disclosure relates to sensing devices.

Sensing devices can include sensor manufactures that can transduce one form of energy into another, e.g., charged coupled devices, piezoelectric materials, or pyroelectric materials. Such sensing devices can include basic control circuitry (e.g., e.g., amplifiers, analog-to-digital converters, input/output circuitry, and the like) on device (e.g., on-chip). The data output by the sensing device can be processed by a processing device in communication with the sensing device.

In particular applications, however, it may be desirable to store data in electronic form within the sensing device. For example, a manufacturer may desire to electrically store serial numbers for sensing devices within the sensing devices. Additionally, if the sensing devices are used in security applications, such as biometric sensing devices, for example, it may be desirable to electrically store data to increase security. For example, it may be desirable to electrically store a private key in the sensing devices, or electrically store particular biometric information, such as fingerprint data for one or more persons, in the sensing devices.

SUMMARY

Disclosed herein in a sensor manufacture with data storage. The electrical properties of the sensor manufacture can be utilized to store data.

In an implementation, a sensing device can include an electrode layer and a sensor manufacture layer defining first and second sides. The sensor manufacture layer can include polarized regions, and the first side of the sensor manufacture layer can be connected to the electrode layer. Electrodes can be connected to the second side of the senor manufacture layer and spaced apart to define data regions in the sensor manufacture layer. Each data region can be polarized according to one of at least two polarization states. The polarization states of the data regions can define the stored data.

Optional advantages and other advantages can be separately realized by the sensor manufacture with the data storage. For example, separate on-chip memory requirements can be reduced. Additionally, data stored within the sensor manufacture can be less susceptible to comprise. For example, if the data are stored according to a polarization of the sensor manufacture, the data store region of the sensor manufacture may not be readily ascertainable by visual inspection or by other inspection means. Such example advantages, however, need not be realized in particular implementations.

DETAILED DESCRIPTION

Figure 1:
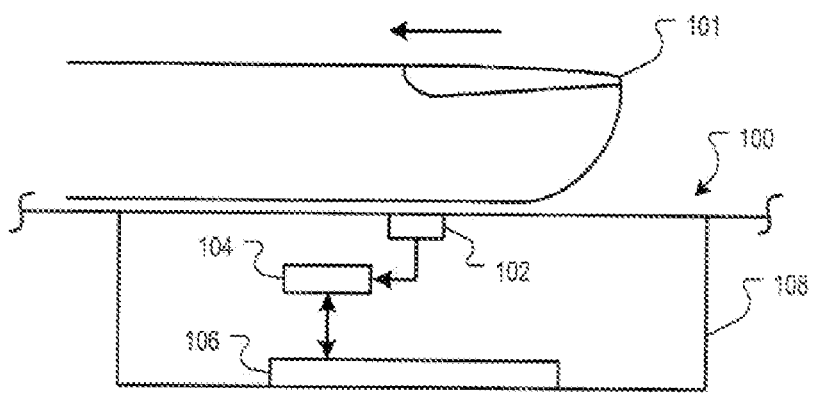
FIG. 1 is a block diagram of an example sensing device.

FIG. 1 is a block diagram of an example sensing device 100. The example sensing device 100 can be a biometric sensing device configured to sense a biometric stimulus, such as the swiping of a finger 101 to read a corresponding fingerprint, for example. The sensing device 100 can implement a different type of sensor, however.

The sensing device 100 can include a sensor manufacture 102 coupled to a processing circuit 104 and an input/output circuit 106. As the finger 101 is pressed and/or swiped on the sensor manufacture 102, the sensor manufacture 102 generates electrical signals based on a characteristic of the fingerprint on the finger 101. The source material of the sensor manufacture 102 can, for example, comprise a layer of polyvinylidene fluoride (PVDF), polyvinylidene fluoride, trifluoroethylene (PVDF-TrFE), polyvinylidene cyanide-vinyl acetate (PVDCN-VAc), or some other transducing material that can produce an electric charge in response to a physical stimulus, such as a biometric stimulus.

The electric signals output by the sensor manufacture 102 are processed by the processing circuit 104 and output through the input/output 106 as biometric data to a processing device, such as a microprocessor executing filtering and recognition algorithms. The example sensing device 100 can generate multiple instances per second of, for example, biometric data, with each instance corresponding to a partial image of a fingerprint. The multiple instances of biometric data can be processed by the processing device to detect overlapping data and generate a complete image of the fingerprint of the finger 101.

In another implementation, the sensor manufacture 102 can be of such proportion to receive an entire fingerprint of the finer 101. In this implementation, the finer 101 can be held stationary against the sensor manufacture 102 and an image of the entire fingerprint can be generated from a single instance of biometric data. Other biometric data collection techniques can also be used.

Figure 2:
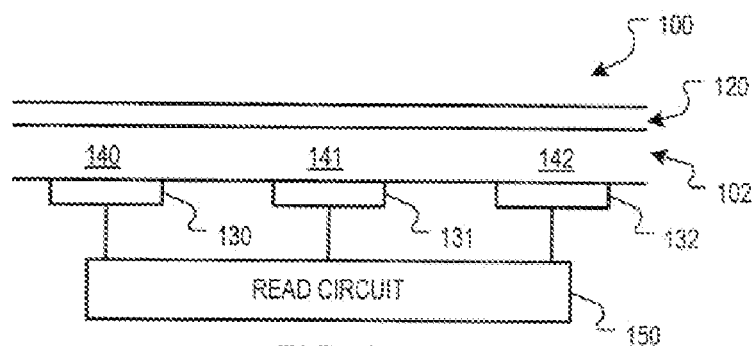
FIGS. 2 and 3 are block diagrams of example data elements defined within the example sensing device.
Figure 3:
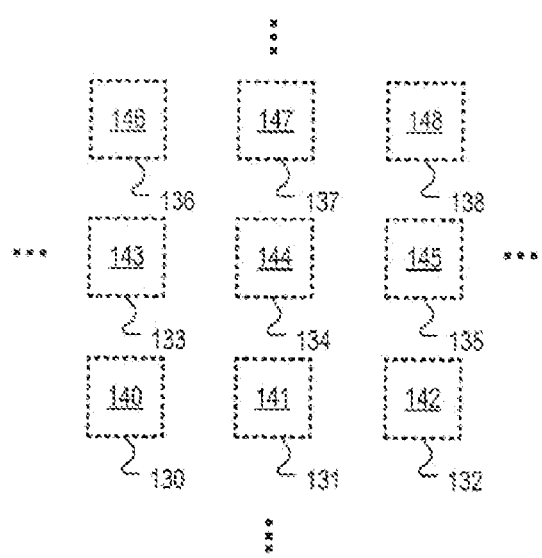

FIGS. 2 and 3 are block diagrams of example data elements defined within the sensor manufacture 102 of the example sensing device 100. The sensor manufacture 102 can, for example, comprises a layer of pyroelectric material fabricated between an upper electrode 120 and a matrix array of lower electrodes as depicted by electrodes 130-138 in FIGS. 2 and 3. Corresponding regions 140-148 are defined by each lower electrode 130-138 and the upper electrode 120. In one implementation, the upper electrode 120 can comprises a single electrode fabricated atop the sensor manufacture 102. In another implementation, the upper electrode 120 can comprises multiple electrodes fabricated atop the sensor manufacture 102, e.g., row electrodes, or column electrodes, or a plurality of electrodes corresponding to the electrodes 130-138.

As shown in FIG. 3, the lower electrodes 130-138 can, for example, be arranged in rows and columns. The number of rows and columns can vary according to the particular implementation of the sensor device 100. For example, the sensor manufacture 102 can comprise a relatively few number of rows and multiple columns and be configured to provide overlapping sections of biometric data during a finger swipe. Alternatively, the sensor manufacture 102 can comprise multiple rows and columns and be configured to provide a single instance of biometric data for an entire fingerprint. In one implementation, the sensor manufacture 102 can be approximately 1.2 centimeters in width and approximately 0.4 millimeters in length, and can comprise 8 rows of electrodes, with each row comprising 232 electrodes. Other configurations can also be used.

A processing circuit 104, such as, for example, a read circuit 150, can be connected to the lower electrodes 130-138. In one implementation, the sensor manufacture 102 can be electrically configured to store data in one or more of the regions 140-148 by altering the electrical characteristics of the sensor manufacture 102. For example, if the sensor manufacture 102 comprises a pyroelectric material, the sensor manufacture 102 can be polarized so that the pyroelectric material generates an electrical signal in response to a thermal transient. The data collected from regions 140-148 during a thermal transient can thus, for example, correspond to pixels. A portion of the sensor manufacture 102, however, can be designated as a memory store. For example, the row defined by the regions 140-142 can be designated as a data store, and the rows defined by the regions 143-145 and 146-148 can be designated as rows of pixels. Thus, in the example sensor manufacture comprising 8 rows of 232 electrodes, the row defined by the regions 140-142 can comprise 232 data regions.

In one implementation, binary values can be associated with a polarization state of each data region. In an implementation, a polarized region can correspond to a binary value of 1, and an unpolarized region can correspond to a binary value of 0. In another implementation, the data regions can be positively polarized, negatively polarized, or unpolarized. Accordingly, in this implementation, a first data value can correspond to a positively polarized region, a second data value can correspond to a negatively polarized region, and a third data value can correspond to an unpolarized region. Other data schemes can also be used.

In an implementation, the data in the data regions can be encoded, for example, according to a reliability scheme (e.g., that includes error correction) or security scheme. For example, the data regions may be arranged according to groups of three and majority weighted for a data value, e.g., the data regions 140, 141 and 142 can all be polarized in the same state and the data of each data region 140, 141 and 142 can be compared to determine the data value stored in the data region group. Thus, if the data regions 140 and 141 correspond to a binary value of 1, and the data region 142 cannot be read or is corrupted, the data value of 1 can still be read from the group. The data stored in the groups of data regions or in the individual data regions can also be stored according to an encryption scheme, such as encryption by a symmetric or asymmetric encryption key. Other storage schemes can also be used.

In an implementation, the regions designated to store the data need not comprise contiguous data regions. For example, data regions can be defined in the sensor manufacture 102 in a systematic or quasi-random manner, e.g., if 232 data regions are to be defined in a sensor manufacture 102 comprising 1,856 regions, then the 232 data regions can be systematically or quasi-randomly distributed within the array of 1,856 region to define a sensor manufacture 102 having 232 data regions and 1,624 pixels.

In an implementation, the regions designated to store data can also be insulated from an external stimulus. For example, if data are stored in the row defined by the regions 140-142, then the row can be insulated from light, heat, or some other external stimulus to which the sensor manufacture 102 is sensitive.

In an implementation, a data region storing a particular value may also provide pixel data in response to an external stimulus. For example, the sensor manufacture 102 may comprise a material that is polarized to generate the electrical signals in response to an external stimulus. After the material is polarized, particular regions may be selected to store data. For example, regions 140-148 may be selected as a data store for eight bits and one parity bit, with polarized regions corresponding to a binary value of 1 and unpolarized regions corresponding to a binary value of 0. Several of the regions 140-148 may thus be depolarized to store the respective values of 1 and 0 in the regions 140-148. Thereafter, the polarized regions of 140-148 in addition to facilitating the storing of a data value, can also provide biometric data in response to an external stimulus. Because the unpolarized regions of 140-148 may not effectively provide biometric data in response to an external stimulus, the processing circuitry 140, e.g., read circuit 150, can be configure to treat the data output corresponding to the unpolarized regions as pixel errors. In this implementation, the data stored in the regions 140-148 can, for example, be read before or after the occurrence of the external stimulus.

In another implementation, positively and negatively polarized data regions can be used to provide pixel data in response to an external stimulus. For example, the sensor manufacture 102 may comprise a material that is polarized to generate the electrical signals in response to an external stimulus. After the material is polarized, particular regions may be selected to store data. For example, regions 140-148 may be selected as a data store for eight bits and one parity bit, with positively polarized regions corresponding to a binary value of 1 and negatively polarized regions corresponding to a binary value of 0. Thus, the entire sensor manufacture 102 can be positively polarized, and then several of the regions 140-148 may thus be negatively polarized to store the respective 0 values. Thereafter, the positively polarized regions of 140-148, in addition, to facilitating the storing of a data value, can also provide biometric data in response to an external stimulus. Likewise, the negatively polarized regions of 140-148, in addition to facilitating the storing of a data value, can also provide biometric data in response to an external stimulus. These signals of the negatively polarized regions can, for example, be inverted to match a corresponding response for a positively polarized region. The processing circuitry 104, e.g., read circuit 150, can be configured to process data corresponding to the negatively polarized regions in an inverted state during a sensing operation, and to process the data corresponding to the negatively polarized regions in a non-inverted state during a read operation. In this implementation, the data stored in the regions 140-148 can, for example, be read before or after the occurrence of the external stimulus.

Other storage and processing schemes can also be used. For example, a column can be configured to store data values; or data values may be stored along the peripheral column and the peripheral rows of the sensor manufacture 102, etc.

Figure 4:
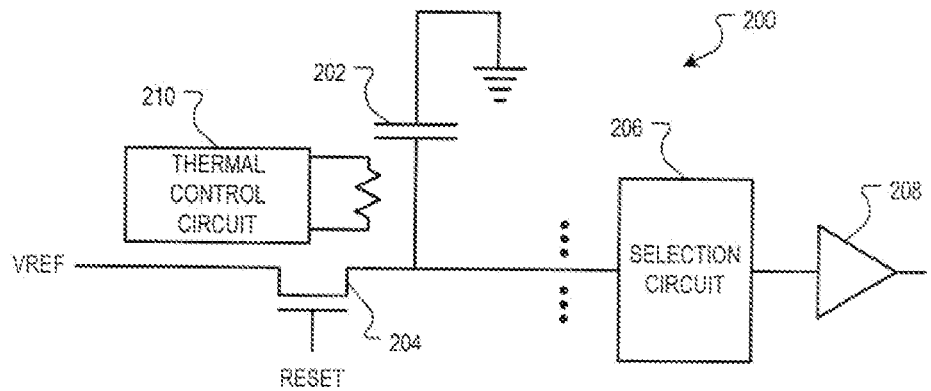
FIG. 4 is a block diagram of an example circuit for reading data stored in a sensor manufacture.

FIG. 4 is a block diagram of an example circuit 200 for reading data stored in a sensor manufacture, such as the sensor manufacture 102. The circuit 200 can, for example, be utilized to facilitate the reading of data stored in a pyroelectric sensor manufacture. A data region can be represented by a capacitor device 202. In one example implementation, a first terminal of the capacitor device 202 can be sustained at a reference ground. For example, during a read operation of the sensor 100, the upper electrode 120 can be sustained at a ground potential.

The second terminal of the capacitor device 202, e.g., a lower electrode, such as electrode 130 of FIG. 2, can be coupled to a gate 204 and a selection circuit 206. During a read operation, the selection circuit 206 can select a particular data region for reading and couple the selected data region to an output amplifier 208.

To initiate a read operation, a thermal control circuit 210 can generate a thermal transient within the data region. If the sensor manufacture 102 within the data region is polarized, the thermal transient will cause a charge to accumulate within the data region. Conversely, if the region is not polarized, the sensor manufacture 102 within the data region will not react to the thermal transient.

In one implementation, a RESET voltage can be applied to the lower electrode of the data region through the gate 204 to set the voltage of the data region to a known reference value, e.g., VREF. Thereafter, the voltage of the data region can change in response to the thermal transient applied by the thermal control circuit 210. In one implementation, the voltage of the data region is measured after an integration time during the thermal transient, e.g., 1 millisecond.

For example, if data are stored within the sensor manufacture 102 by associating a polarized material with a binary value of 1 and an unpolarized material with a binary value of 0, then after the integration time the voltage across a polarized data region can be substantially VRFE+V$\Delta$, as the polarized sensor manufacture generates the addition voltage V$\Delta$ in response to the thermal transient. Likewise, the voltage across an unpolarized data region can be substantially VREF, as the unpolarized sensor manufacture will not react to the thermal transient.

In another implementation, the voltage of the data regions can be measured after an integration time after the thermal transient, e.g., 1 millisecond. In this implementation, the RESET voltage can be applied to the lower electrode of the data region through the gate 204 to set the voltage of the data region to a known reference value, e.g., VREF, after the occurrence of the thermal transient. Thereafter, the data region experiences another thermal transient as it cools in response to the absence of thermal energy provided by the thermal control circuit 210. Thus, after the integration time, the voltage across the polarized data region can be substantially VREF+V$\Delta$, and the voltage across an unpolarized data region can be substantially VREF.

In another implementation, the data can be read after a first integration time during which the data regions are heated, and read again after a second integration time during which the data regions are cooling. The results of the reads can be combined for redundancy and to limit errors.

In another implementation, the data regions can be positively polarized, negatively polarized, or unpolarized, and corresponding data values can be associated with the positively polarized, negatively polarized and unpolarized regions. In this implementation, the voltage across a positively polarized data region after an integration time can be substantially VREF+V$\Delta$; across a negatively polarized region, substantially VREF−V$\Delta$; and across an unpolarized region, substantially VREF. In this implementation, corresponding data values can be associated with the positively polarized, negatively polarized and unpolarized regions. In another implementation, a first binary value can be associated with a positively polarized region, a second binary value can be associated with a negatively polarized region, and the unpolarized region can be ignored, or can be representative of other data, e.g., a data value indicating the beginning or the end of a data block, or a multi-digit binary value, e.g., "00," "01," "10," or "11", for example.

Figure 5:
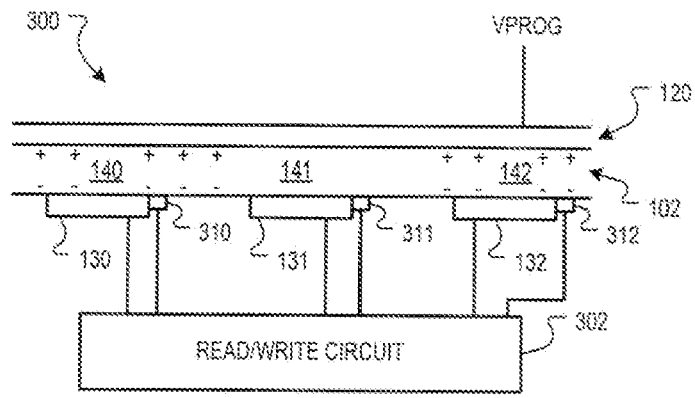
FIG. 5 is a block diagram of an example circuit for reading and storing data in a sensor manufacture.

FIG. 5 is a block diagram of an example circuit 300 for reading and storing data in a sensor manufacture 102. In the example circuit 300 of FIG. 5, the data regions can be either polarized or unpolarized, and corresponding binary values can be associated with the polarized and unpolarized regions.

In one implementation, a read/write circuit 302 can be connected to the lower electrodes, e.g., lower electrodes 130-132. The read/write circuit 302 can, for example, implement the circuit 200 of FIG. 4 to perform read operations. Other read circuits, however, can also be used.

For processing a writing operation, the read/write circuit 302 can, for example, apply a reference potential, e.g., a ground voltage, to the lower electrodes 130-132 that correspond to the data regions 140-142 in which data are to be stored. A program voltage VPROG can, for example, be applied to the upper electrode 120. In an implementation in which the sensor manufacture comprises a pyroelectric layer, the program voltage VPROG can be a voltage that causes the sensor manufacture to polarize when referenced from the reference voltage. The program voltage VPROG can, for example, be applied by connecting a probe to the upper electrode 120, or by coupling the voltage to the upper electrode 120 through a switch, or by some other connection or coupling.

In one implementation, after the sensor manufacture 102 is polarized, the program voltage VPROG is removed and the read/write circuit 302 can, for example, thermally excite one or more data regions above a Curie temperature of the sensor manufacture 102. Upon exceeding the Curie point, the heated region of the sensor manufacture 102 depolarizes. As shown in FIG. 5, in one implementation, each electrode 130, 131 and 132 has an associated heating element 310, 311 and 312, and each heating element 310, 311 and 312 may be individually activated. For example, the heating element 311 was activated to heat the data region 141 above the Curie temperature of the sensor manufacture 102, causing the sensor manufacture 102 to depolarize. According, to three data regions 140-141 can, for example, be read by the read/write circuit 302 to retrieve binary data such as 101 or 010, depending on the association of binary values to the polarization states.

In another implementation, selected resistive elements can be activated while the program voltage VPROG is applied to the top electrode 120. In this implementation, selected data regions of the sensor manufacture 102 are precluded from becoming polarized during the application of VPROG to the top electrode 120.

In one implementation, the heating elements 310-312 can comprise a resistive material. In an implementation, the heating elements 310-312 are proximate to corresponding electrodes 130-132 and thus proximate to corresponding data regions 140-142. Other configurations can also be used. For example, a heating element can be circumferentially disposed around the perimeter of a corresponding lower electrode, or can be located on a corresponding electrode. In another implementation, the heating elements 310-312 can be disposed near the top of the sensor manufacture 102, such as on the top layer of the sensor manufacture 102 or on the upper electrode 120.

In one implementation, the thermal control circuit 210 of the read circuit 200 of FIG. 2 can also be used to implement the heating elements 310-312. In one implementation, the thermal control circuit 210 can apply a first (e.g., short) current pulse or voltage pulse to the heating elements during a read operation, and provide a second (e.g., long) current pulse or voltage pulse during a write operation. In one implementation, the durations are such that the first (e.g., short) duration does not cause the data region to reach the Curie temperature, and the second (e.g., long) duration causes the data region to exceed the Curie temperature and thus depolarize.

In another implementation, the thermal control circuit 210 can apply a low current pulse or low voltage pulse to the heating elements during a read operation, and provide a high current pulse or a high voltage pulse during a write operation. The magnitudes are such that the low pulse does not cause the data region to reach the Curie temperature, and the high pulse causes the data region to exceed the Curie temperature and thus depolarize.

Other thermal control circuits 210 can also be used. For example, separate heating elements and control circuits can be used for read operations and write operations.

The magnitude of the program voltage VPROG can, for example, depend on the thickness of the sensor manufacture 102 layer. For example, if the sensor manufacture 102 comprises a pyroelectric material having a layer thickness of substantially three micrometers, a voltage of about 280 V can be applied across the sensor manufacture 102 layer to polarize the layer.

Figure 6:
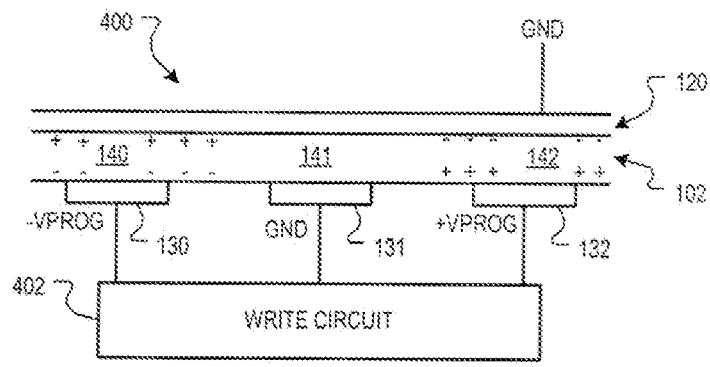
FIG. 6 is a block diagram of example circuit for storing data in a sensor manufacture.

FIG. 6 is a block diagram of example circuit 400 for storing data in a sensor manufacture 102. In this implementation, the data regions can be positively polarized, negatively polarized, or unpolarized, and corresponding data values can be associated with the positively polarized, negatively polarized and unpolarized regions. In another implementation, a first binary value can be associated with a positively polarized region, a second binary value can be associated with a negatively polarized region, and the unpolarized region can be ignored, or can be representative of other data, e.g., a data value indicating the beginning or the end of a data block, or a multi-digit binary value, e.g., "00," "01," "10," or "11", for example.

In one implementation, a write circuit 402 can be connected to the lower electrodes, e.g., lower electrodes 130-132. For processing a writing operation, a reference potential can be applied to the upper electrode 102, and the write circuit 402 can, for example, selectively apply a program voltage VPROG or a reference voltage to the lower electrodes 130-132. In an implementation in which the sensor manufacture comprises a pyroelectric layer, the program voltage VPROG can be a voltage that causes the sensor manufacture 102 to polarize when referenced from the reference voltage. As shown in FIG. 6, the voltages of −VPROG, GND, and +VPROG are applied to the electrodes 130-132, which, in turn, causes the data region 140 to be become positively polarized and the data region 142 to be become negatively polarized. The data region 141, however, remains unpolarized as the potential across the data region 141 is substantially 0 volts.

In another implementation, the write circuit 402 can be configured to provide a single program voltage, e.g., +VPROG. In this example implementation, the sensor manufacture 102 can be either in a common polarized state or an unpolarized state, which can, for example, correspond to binary values.

Figure 7:
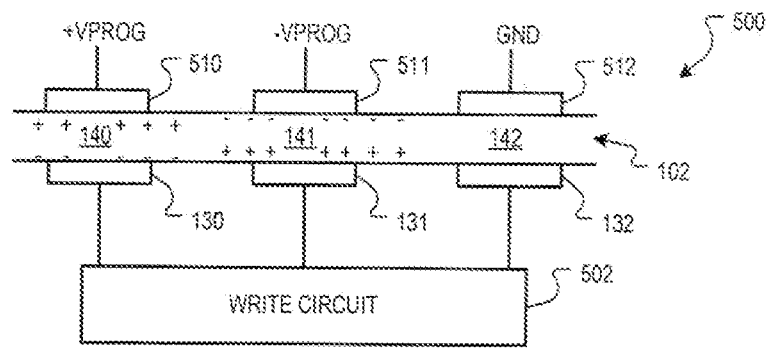
FIG. 7 is a block diagram of another example circuit for storing data in a sensor manufacture.

FIG. 7 is a block diagram of another example circuit 500 for storing data in a sensor manufacture 102. In this implementation, the data regions can be positively polarized, negatively polarized, or unpolarized, and corresponding data values can be associated with the positively polarized, negatively polarized and unpolarized regions. In another implementation, a first binary value can be associated with a positively polarized regions, a second binary value can be associated with a negatively polarized region, and the unpolarized region can be ignored, or can be representative of other data, e.g., a data value indicating the beginning or the end of a data block, or a multi-digit binary value, e.g., "00," "01," "10," or "11", for example.

The example circuit 500 includes top electrodes, e.g., electrodes 510, 511 and 232 disposed on the top surface of the sensor manufacture 102. In one implementation, the top electrodes can comprise electrode rows extending the width of the sensor manufacture 102, e.g., if the sensor device 102 has 8 rows and 232 electrodes columns, then there are 8 separate top electrodes. In another implementation, the top electrodes can comprise electrode columns extending the length of the sensor manufacture 102, e.g., if the sensor device 100 has 8 rows and 232 electrodes columns, then there are 232 separate top electrodes. In another implementation, the top electrodes can comprise corresponding electrodes for each data region, e.g., if the sensor device 102 has 8 rows and 232 electrodes columns, then there are 1,856 separate top electrodes.

For processing a writing operation, a write circuit 502 can, for example, apply a reference potential, e.g., a ground voltage, to the lower electrodes 130-132 that correspond to the data regions 140-142 in which data are to be stored. Program voltages of VPROG or −VPROG can, for example, be applied to the upper electrodes 510-512. In an implementation in which the sensor manufacture 102 comprises a pyroelectric layer, the program voltages can be a voltage that causes the sensor manufacture 102 to polarize when referenced from the reference voltage. The program voltage can, for example, be applied by connecting a probe or probes to the upper electrodes 510-512, or by coupling the voltages to the upper electrode 510-512 through a switch network, or by some other connection or coupling.

As shown, in FIG. 7, the program voltages of +VPROG, −VPROG and the reference voltage GND are applied to the electrodes 510-512, which, in turn, causes the data region 140 to be become positively polarized and the data region 141 to be become negatively polarized. The data region 142, however, remains unpolarized as the potential across the data region 141 is substantially 0 volts.

In another implementation, a single program voltage, e.g., +VPROG, can be applied to the top electrodes 510-512. In this example implementation, the sensor manufacture 102 can be either in a common polarized state or an unpolarized state, which can, for example, correspond to binary values.

Other example circuits can also be used to store data in the sensor manufacture 102. In another implementation, for example, the circuits 400 and 500 of FIGS. 6 and 7 can include heating elements to depolarize data regions or preclude polarization of data regions as described with respect to FIG. 4. For example, positively and negatively polarized regions can be selectively depolarized after programming. The heating elements, e.g., elements 310-312, can be proximate to the lower electrodes 130-132 of FIGS. 6 and 7, or can be proximate to the top electrode 120 of FIG. 6 or the tope electrodes 510-512 of FIG. 7. Other circuit configurations can also be used. By thus conditioning the sensor manufacture 102 as described above, data can be stored electronically in the source material of the sensor manufacture 102.

Figure 8:
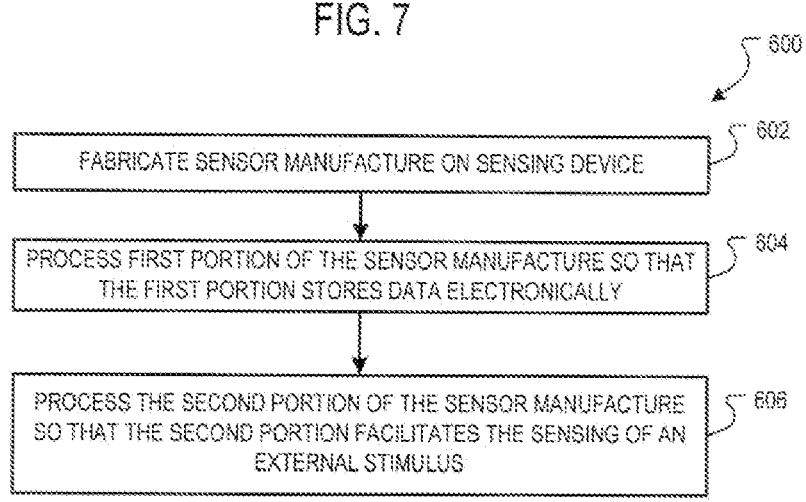
FIG. 8 is a flow diagram of an example process for storing data in a sensor manufacture.

FIG. 8 is a flow diagram of an example process 600 for storing data in a sensor manufacture. The process 600 can, for example, be implemented in the sensor device 100 and in one or more of the example implementations described above.

Stage 602 fabricates a sensor manufacture on a sensing device. For example, the sensor device 100 can be fabricated with the sensor manufacture 102 as shown in FIG. 1.

Stage 604 processes the first portion of the sensor manufacture so that the first portion stores data electronically. For example, the sensor manufacture 102 can undergo polarization, processing by one of the example circuits 300, 400 or 500 as described above.

Stage 606 processes the second portion of the sensor manufacture so that the second portion facilitates the sensing of an external stimulus. For example, the sensor manufacture 102 can be polarized so that the sensor manufacture generates an electrical signal in response to a stimulus, such as a thermal transient caused by a biometric stimulus.

Figure 9:
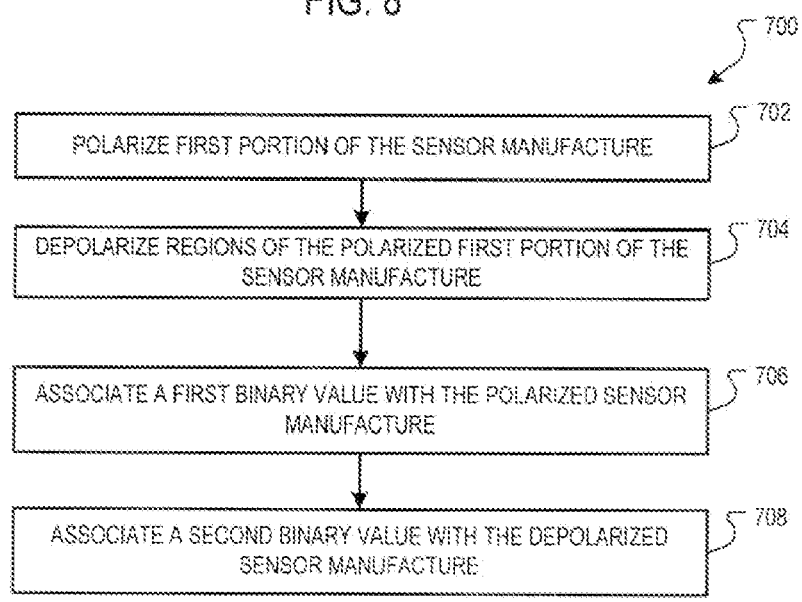
FIG. 9 is a flow diagram of an example process for creating polarized and depolarized regions in a sensor manufacture.

FIG. 9 is a flow diagram of an example process 700 for creating polarized and depolarized regions in a sensor manufacture. The process 700 can, for example, be implemented in the sensor device 100 and in one or more of the example implementations described above.

Stage 702 polarizes the first portion of the sensor manufacture. For example, the sensor manufacture 102 can undergo polarization processing by one of the example circuits 300, 400 or 500 as described above.

Stage 704 depolarizes the regions of the polarized first portion of the sensor manufacture. For example, the sensor manufacture 102 can undergo depolarization processing by one of the example circuits 300, 400 or 500 as described above.

Stage 706 associates a first binary value with the polarized sensor manufacture, and stage 708 associates a second binary values with the depolarized sensor manufacture. For example, the processing circuit 104 of FIG. 1 can be configured to associate a voltage received from the amplifier 208 and corresponding to an unpolarized data region with the binary value of 1, and to associate a voltage received from the amplifier 208 and corresponding to a polarized data region with the binary value of 0.

Figure 10:
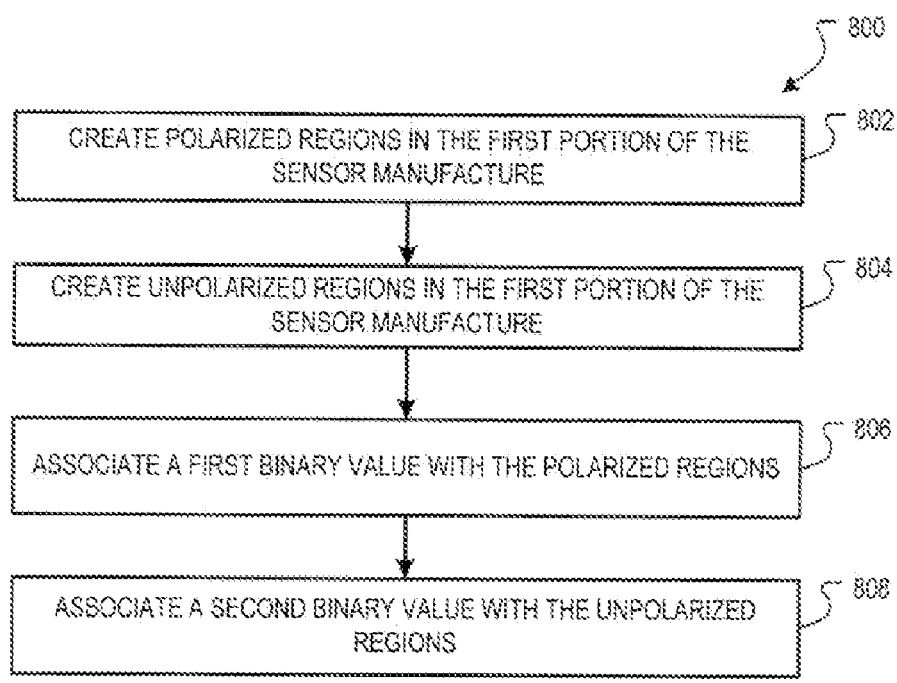
FIG. 10 is a flow diagram of an example process for creating polarized and unpolarized regions in a sensor manufacture.

FIG. 10 is a flow diagram of an example process 800 for creating polarized and unpolarized regions in a sensor manufacture. The process 800 can, for example, be implemented in the sensor device 100 and in one or more of the example implementations described above.

Stage 802 creates polarized regions in the first portion of the sensor manufacture. For example, the sensor manufacture 102 can undergo polarization processing by one of the example circuits 300, 400 or 500 as described above to create polarized regions in the sensor manufacture 102.

Stage 804 creates unpolarized regions in the first portion of the sensor manufacture. For example, the sensor manufacture 102 can undergo depolarization processing by one of the example circuits 300, 400 and 500 as described above to depolarize a polarized region. In another implementation, regions of an unpolarized sensor manufacture 102 can be selectively polarized, which, in turn, creates unpolarized regions that are defined by the polarized regions.

Stage 806 associates a first binary value with the polarized regions, and stage 808 associates a second binary value with the unpolarized regions. For example, the processing circuit 104 of FIG. 1 can be configured to associated a voltage received from the amplifier 208 and corresponding to an unpolarized data region with the binary value of 0, and to associate a voltage received from the amplifier 208 and corresponding to a polarized data region with the binary value of 1.

Figure 11:
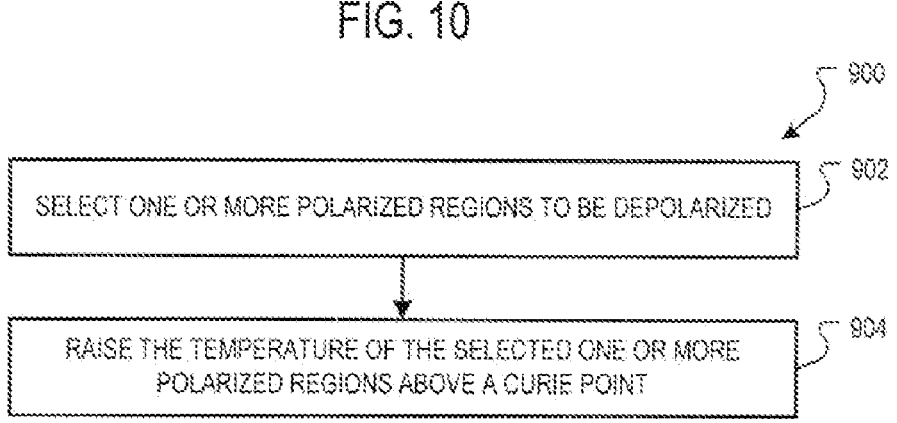
FIG. 11 is an example process for depolarizing a polarized region in a sensor manufacture.

FIG. 11 is a flow diagram of an example process 900 for depolarizing a polarized region in a sensor manufacture. The process 900 can, for example, be implemented in the sensor device 100 and in one or more of the example implementation described above.

Stage 902 selects one or more polarized regions to be depolarized. For example, a polarized region in a sensor manufacture 102 can be selected by the thermal control circuit 210, or by the write circuits 302, 402, and 502 of FIGS. 4-6, to be depolarized.

Stage 904 raises the temperature of the selected one or more polarized regions above a Curie point. For example, a current pulse or voltage pulse can be applied to a heating element to raise the temperature of a polarized region above a Curie temperature of the sensor manufacture 102.

Figure 12:
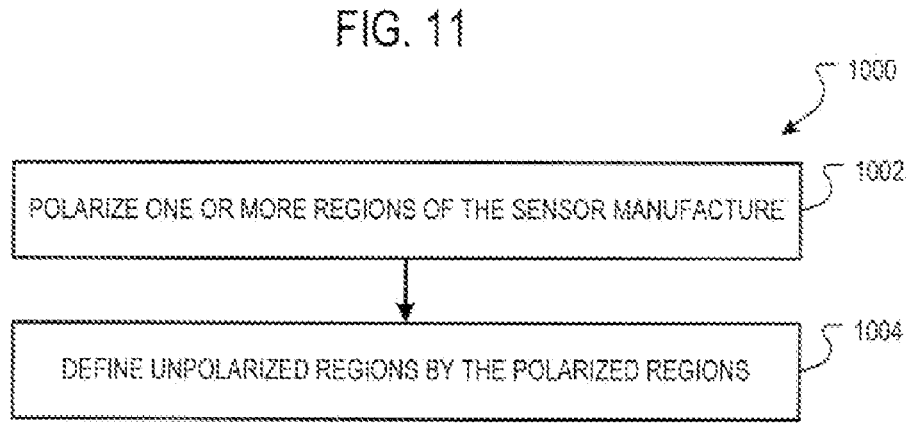
FIG. 12 is an example process for defining depolarized regions in a sensor manufacture.

FIG. 12 is a flow diagram of an example process 1000 for defining depolarized regions in a sensor manufacture. The process 1000 can, for example, be implemented in the sensor device 100 and in one or more of the example implementations described above.

Stage 1002 polarizes one or more regions of the sensor manufacture. For example, the sensor manufacture 102 can undergo polarization processing by one of the example circuits 400 or 500 as described above to create polarized regions in the sensor manufacture 102.

Stage 1004 defines unpolarized regions by the polarized regions. For example, regions of the sensor manufacture 102 that are polarized in FIGS. 6 and 7 can define unpolarized regions, such as polarized regions 140 and 142 defining region 141 as an unpolarized region.

Figure 13:
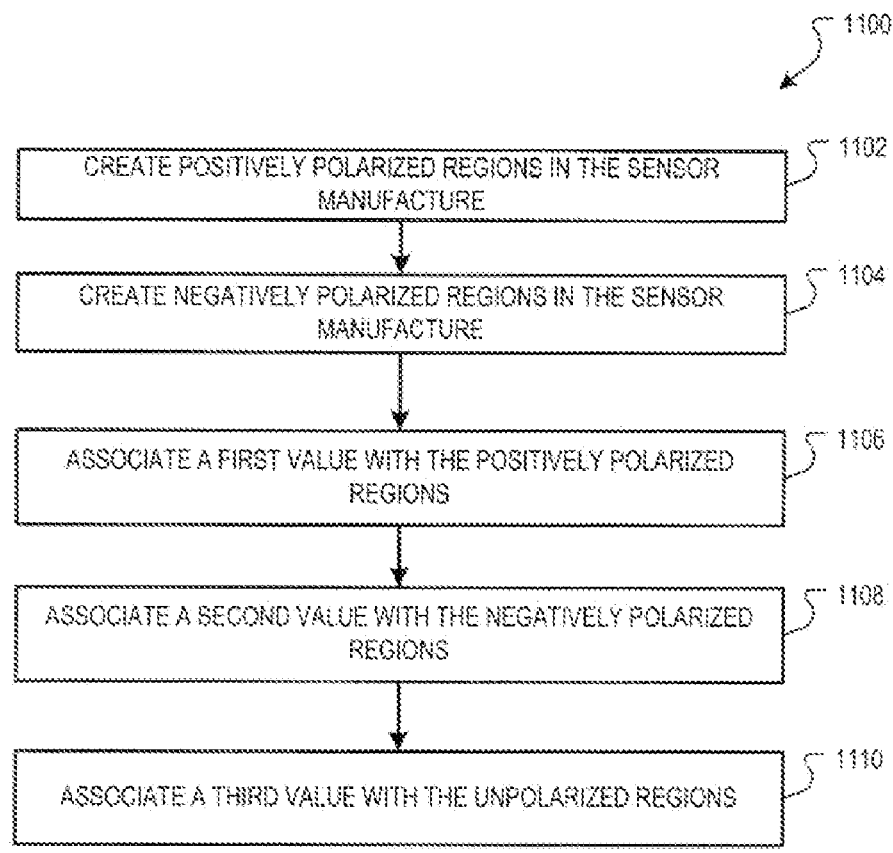
FIG. 13 is an example process for creating positively polarized regions and negatively polarized regions in a sensor manufacture.

FIG. 13 is a flow diagram of an example process 1100 for creating positively polarized regions and negatively polarized regions in a sensor manufacture. The process 1100 can, for example, be implemented in the sensor device 100 and in one or more of the example implementations described above.

Stage 1102 creates positively polarized regions in the sensor manufacture. For example, the sensor manufacture 102 can undergo polarization processing by one of the example circuits 400 or 500 as described above to create positively polarized regions in the sensor manufacture 102.

Stage 1104 creates negatively polarized regions in the sensor manufacture. For example, the sensor manufacture 102 can undergo polarization processing by one of the example circuits 400 or 500 as described above to create negatively polarized regions in the sensor manufacture 102.

Stage 1106 associates a first value with the positively polarized regions. For example, the processing circuit 104 of FIG. 1 can be configured to associate a voltage received from the amplifier 208 and corresponding to positively polarized data region with a first data value.

Stage 1108 associates a second value with the negatively polarized regions. For example, the processing circuit 104 of FIG. 1 can be configured to associate a voltage received from the amplifier 208 and corresponding to negatively polarized data region with a second data value.

Stage 1110 associates a third value with the unpolarized regions. For example, the processing circuit 104 of FIG. 1 can be configured to associate a voltage received from the amplifier 208 and corresponding to an unpolarized data region with a third data value.

Figure 14:
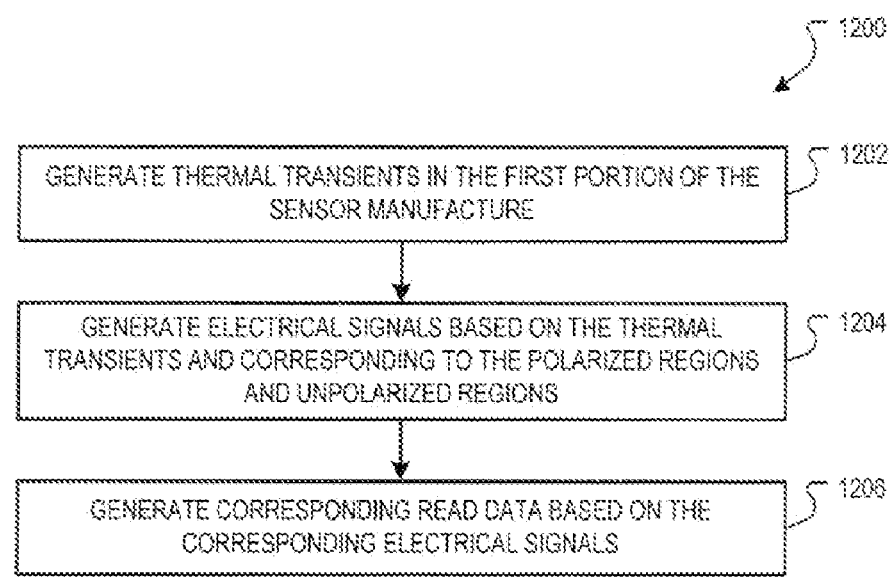
FIG. 14 is a flow diagram of an example process for reading data stored in a sensor manufacture.

FIG. 14 is a flow diagram of an example process 1200 for reading data stored in a sensor manufacture. The process 1200 can, for example, be implemented in the sensor device 100 and in the example circuit 200 of FIG. 4.

Stage 1202 generates thermal transients in the first portion of the sensor manufacture. For example, the thermal control circuit 210 can generate a thermal transient in the data region represented by the capacitive device 202.

Stage 1204 generates electrical signals based on the thermal transients and corresponding to the polarized regions and unpolarized regions. For example, the data region represented by the capacitive device 202 can charge or discharge in response to the thermal transient generated by the thermal control circuit 210.

Stage 1206 generates corresponding read data based on the corresponding electrical signals. For example, the signal output by the amplifier 208 can be processed into a data signal by the processing circuit 104.

Any type of data can be persistently stored in the sensor manufacture 102. For example, the sensor manufacture 102 can be programmed to store a sensor device 100 serial number; and/or a private encryption key to protect against fraud; and/or one or more data sets relating to pre-authorized users, e.g., fingerprints data for cleared individuals, and/or calibration data relating to a sensor parameter, such a temperature; etc.

This written description sets forth the best mode of the invention and provides examples to describe the invention and to enable a person of ordinary skill in the art to make and use the invention. This written description does not limit the invention to the precise terms set forth. Thus, while the invention has been described in detail with reference to the examples set forth above, those of ordinary skill in the art may effect alterations, modifications and variations to the examples without departing from the scope of the invention.

What is claimed is:

1. An apparatus comprising:
   an electrode layer;
   a sensor manufacture layer defining first and second sides, the first side of the sensor manufacture layer connected to the electrode layer, the sensor manufacture layer comprising polarized regions; and
   a plurality of electrodes connected to the second side of the sensor manufacture layer, the plurality of electrodes spaced apart to define data regions in the sensor manufacture layer;
   wherein each data region is polarized according to one of at least two polarization states, and wherein the polarization states of the data regions define stored data.

2. The apparatus of claim 1, wherein:
   the at least two polarization states comprise a polarized state and an unpolarized state.

3. The apparatus of claim 1, wherein:
   the at least two polarization states comprise at least two of a positively polarized state, a negatively polarized state, and an unpolarized state.

4. The apparatus of claim 1, further comprising:
   a plurality of thermal elements associated with each of the plurality of electrodes, the plurality of thermal elements configured to generate thermal energy to induce corresponding electrical signals based on the polarization states of the data regions.

5. The apparatus of claim 4, further comprising:
   a plurality of output amplifiers coupled to the plurality of electrodes, the plurality of amplifiers configured to generate output signals based on the electrical signals.

6. The apparatus of claim 1, wherein:
   the stored data comprises security data.

7. The apparatus of claim 1, wherein:
   the sensor manufacture is integrated in a biometric sensing device configured to sense a biometric stimulus.

8. The apparatus of claim 7, wherein:
   the biometric stimulus comprises an application of a fingerprint to the biometric sensing device.

9. The apparatus of claim 1, wherein:
   the stored data comprises calibration data.

10. The apparatus of claim 1, wherein:
    the electrode layer comprises a plurality of upper electrodes.

11. The apparatus of claim 4, wherein:
    the at least two polarization states comprises a positively state and a negatively polarized state; and further comprising:
    a plurality of output amplifiers coupled to the plurality of electrodes, the plurality of amplifiers configured to generate output signals based on the electrical signals; and
    a processing circuit configured to process data corresponding to the negatively polarized regions in an inverted state during a sensing operation, and to process data corresponding to the negatively polarized regions in a non-inverted state during a read operation.

12. The apparatus of any of claims 1, 4, 8 and 11, wherein:
    the sensor manufacture layer comprises a pyroelectric material.

13. A fingerprint sensor, comprising:
    an electrode layer;
    a pyroelectric sensor layer defining first and second sides, the first side of the pyroelectric sensor layer connected to the electrode layer, the pyroelectric sensor layer comprising polarized regions; and
    a plurality of electrodes connected to the second side of the pyroelectric sensor layer, the plurality of electrodes spaced apart to define data regions in the sensor manufacture layer, wherein each data region is polarized according to one of at least two polarization states, and wherein the polarization states of the data regions define stored data;
    a plurality of thermal elements associated with each of the plurality of electrodes, the plurality of thermal elements configured to generate thermal energy to induce corresponding electrical signals based on the polarization states of the data regions; and
    a plurality of output amplifiers coupled to the plurality of electrodes, the plurality of amplifiers configured to generate output signals based on the electrical signals.

14. The fingerprint sensor of claim 13, wherein:
    the at least two polarization states comprise a positively polarized state and a negatively polarized state.

15. The fingerprint sensor of claim 14, comprising:

a processing circuit connected to the output amplifiers and configured to process data corresponding to the negatively polarized regions in an inverted state during a sensing operation, and to process data corresponding to the negatively polarized regions in a non-inverted state during a read operation.

16. The fingerprint sensor of claim 13, wherein:

the at least two polarization states comprise a polarized state and an unpolarized state.

17. The fingerprint sensor claim 13, wherein:

the at least two polarization states comprise a positively polarized state, a negatively polarized state, and an unpolarized state.

18. The fingerprint sensor of any of claims 13, 15, 16 and 17, wherein:

the stored data comprises security data.

19. The fingerprint sensor of any of claims 13, 15, 16 and 17, wherein:

the stored data comprises calibration data.

* * * * *

UNITED STATES PATENT AND TRADEMARK OFFICE
CERTIFICATE OF CORRECTION

| | |
|---|---|
| PATENT NO. | : 7,385,381 B1 |
| APPLICATION NO. | : 11/682563 |
| DATED | : June 10, 2008 |
| INVENTOR(S) | : Jean-Francois Mainguet |

Page 1 of 1

It is certified that error appears in the above-identified patent and that said Letters Patent is hereby corrected as shown below:

In Column 11, Claim 1, Line 52, please delete "apparatus" and insert -- apparatus, --, therefor.

In Column 12, Claim 11, Line 29, please delete "comprises" and insert -- comprise --, therefor.

In Column 12, Claim 11, Line 29, after "positively", insert -- polarized --.

Signed and Sealed this

Nineteenth Day of August, 2008

JON W. DUDAS
*Director of the United States Patent and Trademark Office*